United States Patent
Kurokawa et al.

(10) Patent No.: US 7,363,084 B2
(45) Date of Patent: Apr. 22, 2008

(54) DEVICE FOR ELECTRICALLY STIMULATING STOMACH

(75) Inventors: Yoshimochi Kurokawa, c/o Graduate School of Medicine, Tohoku University, 1-1, Seiryo-machi, Aoba-ku, Sendai-shi, Miyagi 980-8574 (JP); Makoto Ansai, Sendai (JP)

(73) Assignee: Yoshimochi Kurokawa, Miyagi (JP)

( * ) Notice: Subject to any disclaimer, the term of this patent is extended or adjusted under 35 U.S.C. 154(b) by 26 days.

(21) Appl. No.: 10/540,386

(22) PCT Filed: Dec. 16, 2003

(86) PCT No.: PCT/JP03/16065

§ 371 (c)(1),
(2), (4) Date: Jun. 23, 2005

(87) PCT Pub. No.: WO2004/058349

PCT Pub. Date: Jul. 15, 2004

(65) Prior Publication Data

US 2006/0129200 A1 Jun. 15, 2006

(30) Foreign Application Priority Data

Dec. 25, 2002 (JP) .............................. 2002-373975

(51) Int. Cl.
*A61N 1/00* (2006.01)
(52) U.S. Cl. ..................................................... 607/40
(58) Field of Classification Search ................ 607/2, 607/40; 600/302
See application file for complete search history.

(56) References Cited

U.S. PATENT DOCUMENTS

| 4,044,775 | A | 8/1977 | McNichols |
| 5,540,730 | A | 7/1996 | Terry, Jr. et al. |
| 6,876,885 | B2 * | 4/2005 | Swoyer et al. .............. 607/116 |
| 6,879,859 | B1 * | 4/2005 | Boveja ......................... 607/45 |
| 7,010,351 | B2 * | 3/2006 | Firlik et al. .................... 607/45 |
| 2002/0123774 | A1 * | 9/2002 | Loeb et al. .................... 607/40 |
| 2005/0131487 | A1 * | 6/2005 | Boveja et al. ................. 607/40 |

FOREIGN PATENT DOCUMENTS

| JP | 8-52229 A | 2/1996 |
| WO | WO-94/00188 A1 | 1/1994 |
| WO | WO-96/40367 | 12/1996 |
| WO | WO-97/45160 | 12/1997 |
| WO | WO-01/76690 A1 | 10/2001 |

* cited by examiner

*Primary Examiner*—Scott M. Getzow
(74) *Attorney, Agent, or Firm*—Birch, Stewart, Kolasch & Birch, LLP

(57) ABSTRACT

The present invention provides a gastric electrical stimulation apparatus having (1) a pulse generator located outside of the body, (2) an external coil connecting to the pulse generator, (3) an internal coil which is implanted in the body and receives electricity from the external coil by transcutaneous energy transmission, (4) a waveform rectifier circuit connecting to the internal coil, and (5) electrodes which are positioned in contact with the gastric wall and are connecting to the waveform rectifier circuit. This gastric electrical stimulation apparatus imposes a less burden on users and is capable of providing long pulse stimulation.

2 Claims, 4 Drawing Sheets

DEVICE FOR ELECTRICALLY STIMULATING STOMACH

TECHNICAL FIELD

The present invention relates to a gastric electrical stimulation apparatus for use in treating gastroparesis patients or the like. This apparatus is especially useful as a therapeutic apparatus for gastroparesis patients whose vagus nerve has been cut.

BACKGROUND ART

Gastroparesis (although it is translated into various terms such as gastric incomplete paralysis or gastric contents lingering, the word "gastroparesis" itself is used in this specification) presents symptoms including nausea, vomiting and abdominal bloating, and is a chronic gastric functional disorder which leads to leading to delayed gastric emptying (Hornbuckle K, Barnett J L (2000) J Clin Gastroenterol, 30, 117-124). Gastroparesis may be caused by the cutting of the vagus nerve or by diabetes, but it may also occur without any identifiable cause (idiopathic gastroparesis). Although various conditions are associated in gastroparesis in a complex manner, it is said that abnormalities in gastric myoelectrical activity (GMA), such as increase in dysrhythmia and decrease in the frequency of spike burst, are deeply involved therein (Chen J, McCallum RW (1992) Am J Gastroenterol, 87,477-482). Recently, gastric electrical stimulation has been attracting attention as means for treating drug-resistant, obstinate gastroparesis, and several patent applications have been filed mainly in the United States (see patent documents 1 and 2).

However, in those apparatuses pertaining to gastric electrical stimulation used so far, a circuit to generate stimulation waveforms and a battery (power source) are implanted in the body in the same manner as many implanted-type pacemakers. Therefore, re-operation is necessary for battery replacement. Since major target patients for gastric electrical stimulation are aged persons, such an apparatus requiring a surgical operation periodically imposes a heavy burden on them.

Further, there are two types of stimulations in gastric electrical stimulation: long pulse stimulation (LPS) and short pulse stimulation (SPS). The former is a stimulation with a frequency close to the intrinsic gastric slow wave frequency (IGF) and with a pulse width of 300 ms or more (Bellahsene B E, Lind C D, Schirmer B D, et al. (1992) Am J Physiol, 262,G826-834; Forster J, Sarosiek I, Delcore R, et al. (2001) Am J Surg, 182,676-681; GEMS Study Group. (1996) Gastroenterology, 110,A668; Eagon J C, Kelly K A (1995) Neurogastroenterol Motil, 7,39-45). The latter is a stimulation with a frequency about 4-fold of the intrinsic gastric slow wave frequency and with a pulse width of 1 ms or less (Familoni B O, Abell T L, Nemoto D, et al. (1997) Dig Dis Sci, 42,892-897). Both stimulations have been confirmed to have certain improvement effect on gastroparesis, but actually, apparatuses to provide long pulse stimulation are employed little. This is because long pulse stimulation consumes about 1000 times as much electricity as short pulse stimulation and thus sufficient electricity cannot be secured with the above-mentioned battery-implanted type apparatus.

The above-described problems of the re-operation because of battery expiration and the shortage of electricity in generating long pulse stimulation can be solved by implanting in the body only the circuit to generate stimulation waveforms, locating a power source outside of the body, and supplying electricity through a lead. However, this means that the lead is penetrating the skin, and there is a danger of bacterial infection or the like from the penetration site.

[Patent Document 1] the specification of Japanese Patent No. 2710864

[Patent Document 2] the specification of U.S. Pat. No. 6,115,635

As described so far, the conventional, gastric electrical stimulation apparatus imposed a heavy burden on patients and was virtually impossible to provide long pulse stimulation.

The present invention has been made under such circumstances. It is an object of the present invention to provide a gastric electrical stimulation apparatus which imposes a less burden on patients and is also capable of providing long pulse stimulation.

DISCLOSURE OF THE INVENTION

As a result of extensive and intensive researches toward the solution of the above-described problems, the present inventor has found that supplying electricity to a device implanted in the body by using a transcutaneous energy transmission system makes it unnecessary to make re-operation for battery replacement and makes it possible to provide long pulse stimulation for a long period. The inventor has also found that long pulse stimulation is very effective as means for treating those gastroparesis patients whose vagus nerve has been cut. The present invention has been achieved based on the above findings.

The present invention encompasses the following (A) to (D).

(A) A gastric electrical stimulation apparatus having (1) a pulse generator located outside of the body, (2) an external coil connecting to the pulse generator, (3) an internal coil which is implanted in the body and receives electricity from the external coil by transcutaneous energy transmission, (4) a waveform rectifier circuit connecting to the internal coil, and (5) electrodes which are positioned in contact with the gastric wall and are connecting to the waveform rectifier circuit.

(B) The gastric electrical stimulation apparatus of (A) above, wherein the apparatus is used for gastroparesis patients whose vagus nerve has been cut.

(C) A method of treating gastroparesis, comprising providing long pulse stimulation to gastroparesis patients whose vagus nerve has been cut.

(D) The method of (C) above, wherein the long pulse stimulation is electrical stimulation of square waves with an amplitude of 4 mA, a pulse width of 300 ms and a frequency of 0.03-0.06 Hz.

Hereinbelow, the present invention will be described in detail.

The gastric electrical stimulation apparatus of the invention has a pulse generator, an external coil, an internal coil, a waveform rectifier circuit, and electrodes.

The pulse generator is not particularly limited as long as it is capable of generating a current that can provide effective stimulation to the stomach.

The external coil is not particularly limited as long as it is capable of feeding electricity to the internal coil. Also, the internal coil is not particularly limited as long as it is capable of receiving electricity from the external coil.

The shape of the coil may be, but is not limited to, a flat coil with an outside diameter of 25-35 mm, an inside diameter of 0-20 mm and a thickness of 0.4-0.6 mm. As a wire rod, a copper wire of about 0.1 mm may be used. The number of winding of the coil may be, but is not limited to, 250 to 400. It is preferable to coat the coil surface with silicone, etc. for the purpose of waterproofing, etc. The external coil and the internal coil may or may not have the same shape. In order to increase efficiency in electricity transmission between the coils, ferrite may be provided in the vicinity of the coils. The shape and the location of ferrite are not particularly limited as long as they are capable of increasing efficiency in the electricity transmission. For example, as shown in FIG. 1, a disc-shaped ferrite 1 may be placed on the central part of the external coil 2 and the internal coil 3, and on the external coil 2 on side opposite to the skin.

The waveform rectifier circuit may be any circuit as long as it is capable of rectifying input sine waves, etc. into pulse waves (especially square waves).

The electrodes may be any electrodes as long as they are capable of providing effective electrical stimulation to the stomach. For example, electrodes for use in heart pacing may be used.

Hereinbelow, the gastric electrical stimulation apparatus of the invention will be described in reference to FIG. 2. By feeding a sine wave current from the pulse generator 4 to the external coil 2, electromagnetic induction between the coils generates a sine wave current in the internal coil 3. This sine wave current is converted into a pulse current through the waveform rectifier circuit 5, and this pulse current gives electric stimulation to the stomach through the electrodes 6.

The gastric electrical stimulation apparatus of the invention may be used for treating diseases such as gastroparesis. Prior to the treatment, the internal coil, the waveform rectifier circuit, and electrodes for gastric stimulation are implanted in the body in advance. The sites of implanting for the internal coil and the waveform rectifier circuit are not particularly limited. Usually, it is preferable to implant them subcutaneously in the precordial or epigastric region. The electrodes for gastric stimulation are positioned in contact with the gastric wall. Usually, they are positioned on the anterior gastric wall along the greater curvature in the upper part of the stomach. The distance between the electrodes is preferably about 5-10 mm.

Treatment is performed by feeding a sine wave current from the pulse generator and bringing the external coil close to the site where the internal coil is implanted in the patient's body. The frequency and amplitude of the sine wave current may be appropriately selected so that electrical stimulation effective on the stomach (long pulse stimulation and short pulse stimulation) is generated. Usually, when long pulse stimulation is to be given, the frequency and amplitude are 0.03-0.06 Hz and 4-6 mA, respectively. When short pulse stimulation is to be given, the frequency and amplitude are 0.12-0.24 Hz and 2-4 mA, respectively.

The gastric electrical stimulation apparatus of the present invention is suitable for providing long pulse stimulation. Further, as described later, long pulse stimulation is effective for gastroparesis patients whose vagus nerve has been cut. Therefore, the gastric electrical stimulation apparatus of the present invention is especially useful as a therapeutic apparatus for gastroparesis patients whose vagus nerve has been cut.

BEST MODES FOR CARRYING OUT THE INVENTION

Hereinbelow, the present invention will be described in more detail with reference to the following Example.

1. Experimental Methods (1) Electrode Implantation

Figure 1:
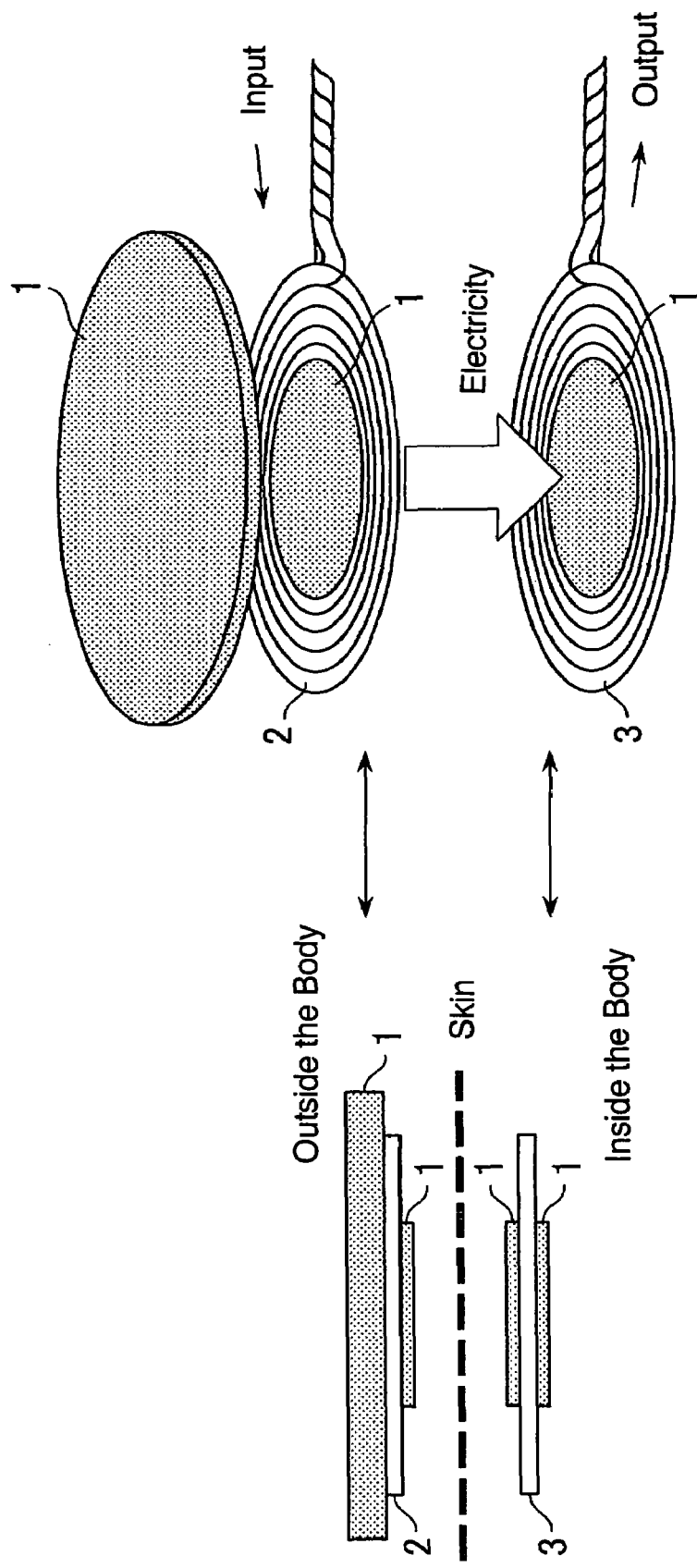
FIG. 1 is a diagram showing the positions of ferrite against the external coil and the internal coil.
Figure 2:
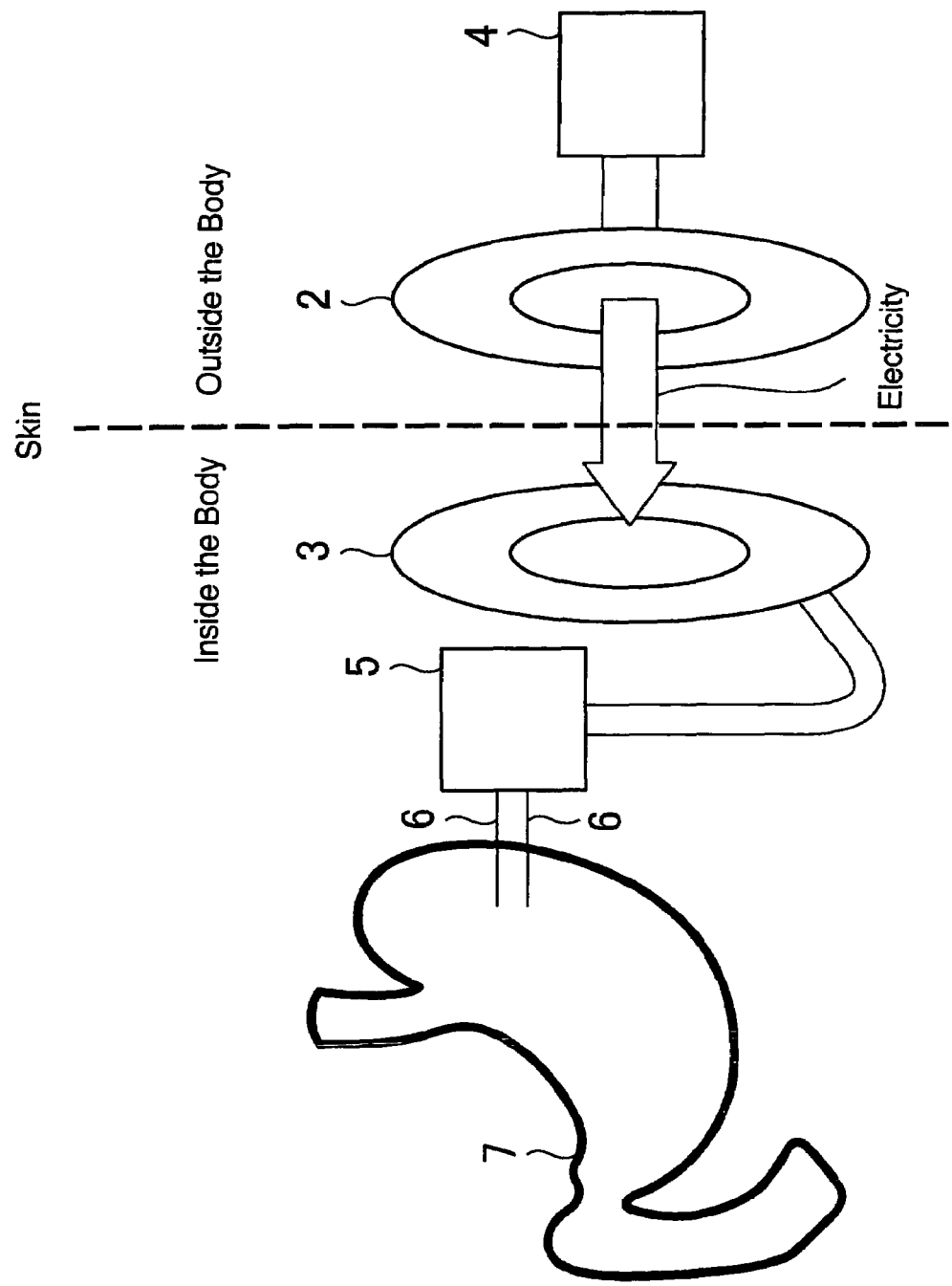
FIG. 2 is a schematic diagram of the gastric electrical stimulation apparatus of the present invention.
Figure 3:
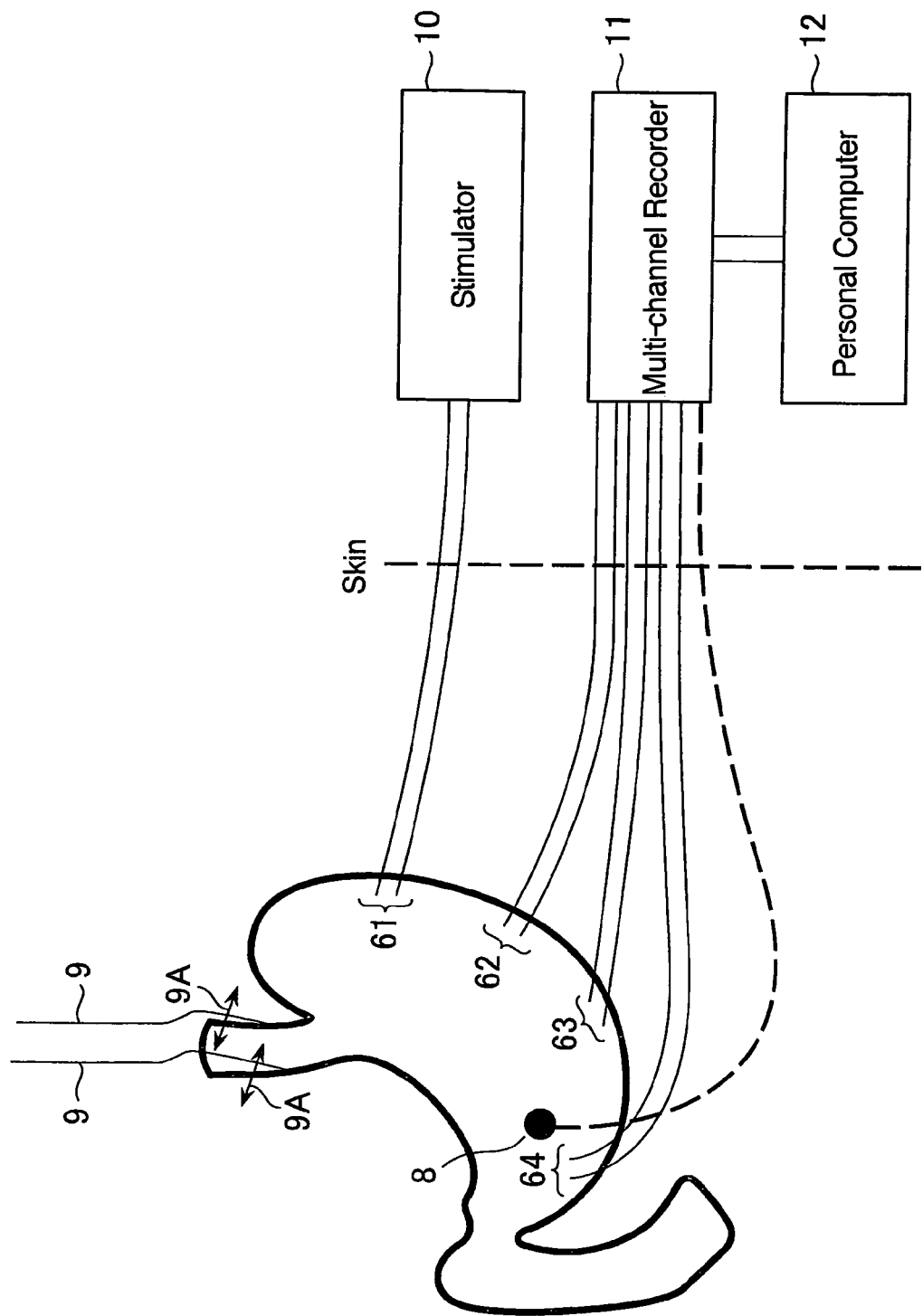
FIG. 3 is a layout of the electrodes and various instruments used in the Example.

Six female beagle dogs (8-9.5 kg in body weight) were used in this experiment. Surgical operation for electrode implantation was carried out under general anesthesia after fasting for more than 12 hr. Briefly, ketamine was administered intravenously at 20 mg/kg, and then endotracheal intubation was performed, followed by respiration control with a respirator. Anesthesia was maintained with inhalation anesthetic isoflurane (about 2%). Midline laparotomy was performed in the epigastrium, and 4 pairs of 28 gauge stainless heart-pacing wire (A&E Medical Farmingdale) were implanted from the serosa side of the stomach into the muscularis propria of the anterior gastric wall on the greater curvature side. The distance between each two electrodes forming a pair was 1 cm. Four pairs of electrodes located from the mouth side were designated ch1 (61), ch2 (62), ch3 (63) and ch4 (64). The distance between adjacent pairs was 4 cm. The electrode located on the utmost anus side was 2 cm distant from the pyloric ring. A force transducer 8 (Star Medical) which is a pressure sensor for measuring contractive force was sutured onto the serosa of the anterior gastric wall, 4 cm distant from the pyloric ring. A Teflon-coated lead thereof was brought out from the ventral part of the epigastrium to the outside of the abdominal cavity, and then brought out of the body from the right part of the chest subcutaneously (FIG. 3).

After completion of the experiment in the presence of the vagus nerve, vagotomy was performed. Anesthetization was carried out in the same manner as in the first surgical operation. Midline laparotomy was performed in the epigastrium, and all the trunks of the vagus nerve 9 present around the esophagus were excised over approx. 2 cm immediately below the diaphragm (FIG. 3; site of excision: 9A).

(2) Electrical Stimulation

Experiments were started 7 days or more after the surgical operation when dogs were judged as completely recovered. Experiments were performed with an interval of 2 days or more on the same individual. After fasting for more than 12 hrs, 400 g of dog food (340 Kcal; wet food containing beef, vegetables, etc.) was fed. Then, measuring was started 30 min thereafter. First, baseline gastric myoelectrical activity and contractive force were measured for 30 min. Subsequently, similar measurement was carried out for 30 min without stimulation in control group and with electrical stimulation in experimental groups. All experiments were performed on conscious animals.

The electrodes located on the utmost mouth side were connected to a stimulator 10 (DPS-1200D; Dia Medical System), and electrical stimulation was performed using square waves (FIG. 3). Stimulation conditions were as follows: for long pulse stimulation, the frequency was 1.1-fold of the intrinsic gastric slow wave frequency, the pulse width was 550 ms and the pulse amplitude was 4 mA; for short pulse stimulation, the frequency was 20 cmp, the pulse width was 0.3 ms, and the pulse amplitude was 2 mA.

The measurement of gastric myoelectrical activity and contractive force were measured before and after the cutting of the vagus nerve; and each measurement was performed under the three conditions of control, long pulse stimulation and short pulse stimulation. In addition to these measurements, gastric myoelectrical activity and contractive force after the cutting of the vagus nerve were measured under long pulse stimulation with an apparatus using the transcutaneous energy transmission system.

(3) Data Analysis (A) Recording of Gastric Myoelectrical Activity

Gastric myoelectrical activity was recorded by bringing the leads of these electrodes for recording out of the body and connecting them to a multi-channel recorder 11 (Acknowledge, Biopac Systems) (FIG. 3). The recording waveforms were displayed on the monitor of a personal computer 12 and stored in the hard disc simultaneously (FIG. 3). Low cut off frequency was set at 0.05 Hz and high cut off frequency at 35 Hz. In the analysis of slow waves, the recordings were filtered with a frequency of 1 Hz through a low pass filter 15 using a software, followed by re-sampling at a frequency of 4 Hz.

Gastric myoelectrical activity recordings were subjected to running spectral analysis using the following two parameters.

(i) Percentage of Normal Slow Waves (NSW)

It is said that normal slow waves of dog stomach are 3.5-7 cpm. First, the recorded data of g myoelectrical activity were divided into 1-min segments. In each of these segments, if the frequency at which the intensity of the running spectrum reaches the maximum (i.e. predominant frequency) is present within the range of 3.5-7 cpm, the segment was judged "normal slow wave". The ratio of normal slow waves in the observation period was defined as percentage of normal slow waves, which is a parameter reflecting the regularity of gastric myoelectrical activity.

(ii) Percentage of Slow Wave Coupling

When the difference in predominant frequency of 1-min segment between two different channels is less than 0.5 cpm, the slow waves of these two channels were regarded as "coupling". The ratio of coupling in the observation period was defined as percentage of slow wave coupling, which is a parameter reflecting the transmission of slow waves from the mouth side to the anus side.

(B) Recording of Contractive Force

The contractive force was recorded by connecting the force transducer to the multi-channel recorder (Acknowledge, Biopac Systems) in the same manner as in the recording of gastric myoelectrical activity. After filtering in the same manner, waveforms sampled with a frequency of 20 Hz were re-sampled with a sampling frequency of 1 Hz. Then, the area under the curve (AUC) of recorded waveforms was calculated, followed by evaluation of contraction force with the area under the curve per unit time.

In order to evaluate the effect of gastric electrical stimulation, the effect was evaluated with the ratio of alteration from the baseline for the above-mentioned parameter. Briefly, alteration ratio at variable X is expressed as ▯X, and the baseline value and the value under electrical stimulation are expressed as X1 and X2, respectively. Then, ▯X is defined as X2/X1. The values of alteration ratio ▯X in individual groups were used as targets of evaluation.

(4) Transcutaneous Energy Transmission System

The coils used in the transcutaneous energy transmission system were multilayer wound coils made of a copper wire 0.1 mm in diameter. A magnetic material of Mn—Cu—Zn (ferrite) is used on the external surfaces of the coils. The outer sizes of the external coil and the internal coil are 42 mm long, 32 mm wide and 6 mm thick.

Prior to the experiment of gastric electrical stimulation using the transcutaneous energy transmission system, a surgical operation was performed to implant the internal coil. A pocket was created subcutaneously in the left part of the chest, into which the internal coil was implanted and fixed.

Figure 4:
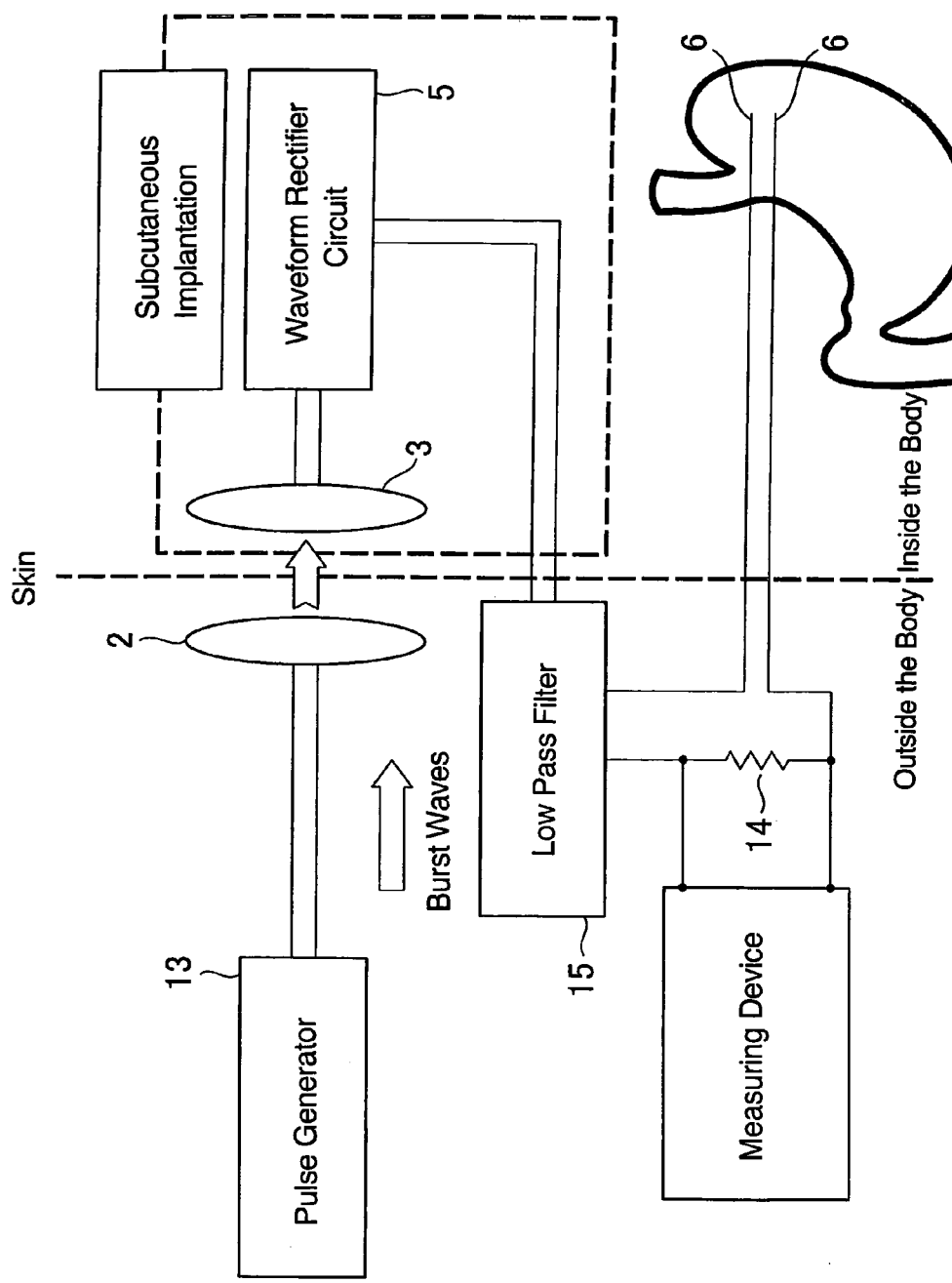
FIG. 4 is a block diagram of the transcutaneous energy transmission system.

A block diagram of the transcutaneous energy transmission system is as shown in FIG. 4. In order to produce stimulation waveforms of long pulse stimulation from the current generated by the pulse generator 13 (NF Corporation; Wave Factory 1946 Multifunction Synthesizer), sine wave burst waveforms of 100 kHz corresponding to the relevant stimulation frequency and pulse width were input into the external coil 2. The induced voltage in the external coil 2 was passed through the waveform rectifier circuit 5 to thereby rectify sine waves into square waves. Further, in order to measure the amount of current running in the electrodes 6 implanted in the stomach when electrical stimulation is provided, the wiring of the electrodes 6 was once brought out of the body and a shunt resistance 14 was provided in the course. Then, the wiring was returned into the body. The voltage induced at the ends of this shunt resistance was amplified, followed by measuring the current value. The electrode portion from the shunt resistance to the tunica muscularis ventriculi is made of a stainless wire, and the remaining part is made of a copper wire.

When electrical stimulation was provided, the voltage was adjusted with the pulse generator so that the generated current has a frequency of IGF×1.1, a pulse width of 550 ms, and a measured current of 4 mA. Further, during the measurement, generated stimulation waveforms were observed with an oscilloscope in real time.

(5) Statistical Analysis

Statistical analysis was performed as follows. In the analysis between three groups, first, repeated measures analysis of variance (ANOVA) was used. When there was a significant difference, multiple comparison test was performed by Fisher's PLSD. In each test, the level of significance was set at $p<0.05$. All the measured values were expressed as (mean±standard deviation).

2. Experimental Results

No apparent changes such as vomiting were observed in any dog during stimulation.

When it was impossible to entrain waves in long pulse stimulation, changing the amplitude to 6 mA made it possible to entrain slow waves within 5 min in every experiment. Further, since an artifact resulted from gastric electrical stimulation mixed into ch2 which is close to the stimulation channel, only ch3 and ch4 were analyzed. After the cutting of the vagus nerve, vomiting was confirmed twice or more in every dog. An average 1.3 kg of weight loss was observed one month after the surgical operation.

(1) Effect of Long Pulse Stimulation and Short Pulse Stimulation before the Cutting of the Vagus Nerve With respect to the contractive force before the cutting of the vagus nerve, while the alteration ratio in the area under the curve was 0.93±0.20 in control group, that ratio in long pulse stimulation group was 0.79±0.23 and that ratio in short pulse group. The alteration ratio was increased significantly in short pulse group. The alteration ratios in the percentage of normal slow waves were 0.92±0.18 in control group, 1.24±0.78 in long pulse stimulation group, and 0.95±0.20 in short pulse stimulation group. The alteration ratios in the percentage of slow wave coupling were 0.92±0.23 in control group, 1.06±0.71 in long pulse stimulation group, and 1.36±0.46 in short pulse stimulation group. Thus, no significant difference was observed in ANOVA.

(2) Effect of Long Pulse Stimulation and Short Pulse Stimulation after the Cutting of the Vagus Nerve With respect to the contractive force after the cutting of the vagus nerve, the alteration ratios in the area under the curve were 1.00±0.22 in control group, 1.23±0.22 in long pulse stimulation group and 0.96±0.09 in short pulse stimulation group. Thus, long pulse stimulation group showed an increasing tendency, though no significant difference was observed in ANOVA (p=0.08). The alteration ratios in the percentage of normal slow waves were 0.96±0.07 in control group, 1.31±0.39 in long pulse stimulation group, and 0.93±0.10 in short pulse stimulation group. Thus, long pulse stimulation group showed a significant increase compared to the other groups. The alteration ratios in the percentage of slow wave coupling were 1.02±0.13 in control group, 1.42±0.31 in long pulse stimulation group, and 1.08±0.46 in short pulse stimulation group. Thus, long pulse stimulation group showed an increasing tendency, though no significant difference was observed in ANOVA (p=0.14).

(3) Effect of Gastric Electrical Stimulation by Transcutaneous Energy Transmission System With respect to the long pulse stimulation after the cutting of the vagus nerve, gastric electrical stimulation with the conventional stimulation apparatus and gastric electrical stimulation by transcutaneous energy transmission system were compared to control group. As to contractive force, the alteration ratios in the area under the curve were 1.00±0.22 in control group, 1.23±0.22 in conventional apparatus group and 1.11±0.47 in transcutaneous energy transmission system apparatus group. Thus, no significant difference was observed. The alteration ratios in the percentage of normal slow waves were 0.96±0.07 in control group, 1.31±0.39 in conventional apparatus group, and 1.39±0.40 in transcutaneous energy transmission system apparatus group. Thus, conventional apparatus group and transcutaneous energy transmission system apparatus group showed a significant increase compared to control group. Further, no significant difference was found between conventional apparatus group and transcutaneous energy transmission system apparatus group. The alteration ratios in the percentage of slow wave coupling were 1.02±0.13 in control group, 1.42±0.31 in conventional apparatus group, and 1.63±0.57 in transcutaneous energy transmission system apparatus group. Thus, transcutaneous energy transmission system apparatus group showed a significant increase compared to control group, but there was no significant difference compared to conventional apparatus group.

The present specification encompasses the contents disclosed in the specification and/or drawings of Japanese Patent Application No. 2002-373975 based on which the present application claims priority. All publications, patents and patent applications cited herein are incorporated herein by reference in their entity.

INDUSTRIAL APPLICABILITY

The gastric electrical stimulation apparatus of the present invention is useful in treating diseases such as gastroparesis. Further, long pulse stimulation is effective for treating gastroparesis patients whose vagus nerve has been cut, and the apparatus of the present invention is capable of providing this long pulse stimulation for a long period of time. Therefore, the apparatus of the present invention is especially useful as a therapeutic apparatus for gastroparesis patients whose vagus nerve has been cut.

The invention claimed is:

1. A method for treating gastroparesis, comprising:
    connecting a pulse generator to an external coil;
    receiving electricity at an internal coil from the external coil by at least transcutaneous energy transmission, the internal coil being implantable in a gastroparesis patient;
    connecting a waveform rectifier circuit to the internal coil;
    connecting electrodes to the waveform rectifier circuit, the electrodes are capable of being positioned in contact with a gastric wall;
    feeding a sine wave current from the pulse generator when the external coil is positioned at an external site in proximity to where the internal coil is implanted so that an electrical stimulation is effective on the stomach; and
    selecting a frequency and amplitude of the sine wave current so that the electrical stimulation is providing long pulse stimulation with a pulse width of 300 ms or more to the gastroparesis patient whose vagus nerve has been cut.

2. The method according to claim 1, wherein the long pulse stimulation is electrical stimulation of square waves with an amplitude of 4 mA, and a frequency of 0.03-0.06 Hz.

* * * * *